(12) United States Patent
Zhang et al.

(10) Patent No.: US 12,714,435 B2
(45) Date of Patent: Aug. 25, 2026

(54) EMBOLIC AGENT AND PREPARATION METHOD THEREFOR

(71) Applicant: NEUROGUARD MEDICAL (SHANGHAI) CO., LTD., Shanghai (CN)

(72) Inventors: Shuo Zhang, Shanghai (CN); Rui Yang, Shanghai (CN); Liang Cai, Shanghai (CN); Shaojun Qian, Shanghai (CN); Hua Yu, Shanghai (CN)

(73) Assignee: NEUROGUARD MEDICAL (SHANGHAI) CO., LTD., Shanghai (CN)

( * ) Notice: Subject to any disclaimer, the term of this patent is extended or adjusted under 35 U.S.C. 154(b) by 514 days.

(21) Appl. No.: 18/255,485

(22) PCT Filed: Nov. 15, 2021

(86) PCT No.: PCT/CN2021/130762
§ 371 (c)(1),
(2) Date: Jun. 1, 2023

(87) PCT Pub. No.: WO2022/142787
PCT Pub. Date: Jul. 7, 2022

(65) Prior Publication Data

US 2024/0016498 A1 Jan. 18, 2024

(30) Foreign Application Priority Data

Dec. 31, 2020 (CN) ......................... 202011624579.0

(51) Int. Cl.
*A61B 17/12* (2006.01)
*A61B 17/00* (2006.01)

(52) U.S. Cl.
CPC .... *A61B 17/1215* (2013.01); *A61B 17/12113* (2013.01); *A61B 2017/00004* (2013.01); *A61B 2017/00526* (2013.01)

(58) Field of Classification Search
CPC .......... A61B 17/1215; A61B 17/12113; A61B 17/12154; A61B 17/12031;
(Continued)

(56) References Cited

U.S. PATENT DOCUMENTS 5,226,911 A * 7/1993 Chee ................ A61B 17/12145 606/198
5,382,260 A * 1/1995 Dormandy, Jr. ... A61B 17/1215 606/151
(Continued)

FOREIGN PATENT DOCUMENTS

CN 102119004 A 7/2011
CN 104739478 A 7/2015
(Continued)

*Primary Examiner* — Tan-Uyen T Ho
*Assistant Examiner* — Osama Nemer
(74) *Attorney, Agent, or Firm* — MUNCY, GEISSLER, OLDS & LOWE, P.C.

(57) ABSTRACT

An embolization member (10) and a method for fabricating it are disclosed. The embolization member (10) includes a tubular first helical member (100) comprising a lumen (110), a second helical member (120) sleeved over an outer surface of the first helical member (100) and a securing member (170) at least partially disposed within the lumen (110) of the first helical member (100). The first helical member (100) includes a radiopaque material, and the second helical member (120) includes a bioabsorbable material. The securing member (170) is coupled at opposite ends thereof to respective opposite ends of the second helical member (120), so as to secure the first helical member (100) to the second helical member (120). The securing member (170) incorporated in the double-layer structure of the emboliza- (Continued)

tion member (10) not only imparts degradability to the embolization member (10), which can mitigate a possible mass effect that it may exert, but also enable it to maintain good structural stability within an aneurysm.

20 Claims, 2 Drawing Sheets

(58) Field of Classification Search
CPC .... A61B 17/12145; A61B 2017/00004; A61B 2017/00526; A61B 2017/0092; A61B 2090/3966
See application file for complete search history.

(56) References Cited

U.S. PATENT DOCUMENTS

| | | | | | |
|---|---|---|---|---|---|
| 5,509,642 | A * | 4/1996 | Wells | A47C 27/07 | 5/256 |
| 5,749,891 | A * | 5/1998 | Ken | A61B 17/12113 | 606/191 |
| 5,935,145 | A * | 8/1999 | Villar | A61B 17/1215 | 606/205 |
| 6,027,461 | A * | 2/2000 | Walker | A61M 25/0009 | 600/585 |
| 6,179,857 | B1 * | 1/2001 | Diaz | A61B 17/12022 | 606/1 |
| 6,280,457 | B1 * | 8/2001 | Wallace | A61B 17/12022 | 606/191 |
| 6,331,188 | B1 * | 12/2001 | Lau | A61F 2/915 | 606/198 |
| 10,869,673 | B2 * | 12/2020 | Zhang | A61B 17/12145 | |
| 2004/0098028 | A1 * | 5/2004 | Martinez | A61B 17/1219 | 606/200 |
| 2005/0192621 | A1 | 9/2005 | Wallace et al. | | |
| 2006/0004440 | A1 * | 1/2006 | Stinson | A61B 17/1214 | 623/1.34 |
| 2006/0079926 | A1 | 4/2006 | Desai | | |
| 2010/0036412 | A1 * | 2/2010 | Porter | A61B 17/12154 | 606/191 |
| 2011/0245861 | A1 * | 10/2011 | Chen | A61B 17/12154 | 606/200 |
| 2011/0293877 | A1 * | 12/2011 | Wolters-Zuur | B29C 48/05 | 428/97 |
| 2013/0338702 | A1 * | 12/2013 | Desai | A61B 17/32056 | 606/200 |
| 2015/0196304 | A1 * | 7/2015 | Rabkin | C22F 1/006 | 148/563 |
| 2017/0245865 | A1 * | 8/2017 | Jones | A61B 17/12154 | |

FOREIGN PATENT DOCUMENTS

| | | | |
|---|---|---|---|
| CN | 107773283 | A | 3/2018 |
| CN | 110179516 | A | 8/2019 |
| CN | 111870303 | A | 11/2020 |
| CN | 112641484 | A | 4/2021 |
| CN | 112656476 | A | 4/2021 |
| CN | 113303859 | A | 8/2021 |
| CN | 113303860 | A | 8/2021 |
| CN | 215273059 | U | 12/2021 |

* cited by examiner

EMBOLIC AGENT AND PREPARATION METHOD THEREFOR

CROSS-REFERENCES TO RELATED APPLICATION

This application claims the priority of Chinese patent application number 202011624579.0, filed on 31 Dec. 2020 and entitled "EMBOLIC AGENT AND PREPARATION METHOD THEREFOR", the entire contents of which are incorporated herein by reference.

TECHNICAL FIELD

The present invention relates to the field of medical devices and, in particular, to an endovascular embolization member and a preparation method therefor.

BACKGROUND

Intracranial aneurysms are pathological bulges in intracranial artery walls, which form tumor-like lesions. According to surveys, the incidence of intracranial aneurysms has showed an increasing trend in recent years. Coupled with the high mortality and disability rates of this disease, there is an urgent need to improve the cure rate of intracranial aneurysms.

With the development of imaging and material science, surgical treatment of intracranial aneurysms by coil embolization is gaining more and more attention and importance thanks to its advantages including less trauma, lower risk and fewer complications. At present, coils used for such interventional therapy are mostly made of metallic materials. When packed into the cavity of an intracranial aneurysm, such a coil can effectively change the direction of blood flow, reducing pressure on the wall of the aneurysm. At the same time, it can induce thrombosis and promote endothelialization at the neck of the aneurysm, thereby providing a therapeutic effect to the aneurysm.

However, the application of these traditional metal embolization coils to the treatment of large and giant aneurysms is limited because, with their permanent presence in aneurysm cavities, they may push on or otherwise adversely affect the surrounding nerves and tissues due to mass effects. When filled in aneurysms, coils made of bioabsorbable materials will be degraded and absorbed. As a result, when pushed on by the surrounding tissues, the aneurysms will gradually shrink, leading to reduced mass effects. Moreover, the bioactive materials can accelerate the formation of fibrocytes at the aneurysm necks, facilitating the regeneration of vascular smooth muscle. Therefore, such coils have received extensive attention.

Currently, coils containing degradable/absorbable material are still at a proof-of-concept stage and there are no feasible products on the market. According to surveys, coils made of absorbable bioactive materials usually have good X-ray transparency. Consequently, in practice, their radiographic visibility during advancement is poor, increasing surgeons' difficulty in manipulation. In addition, a few reports have proposed the addition of radiopaque components to degradable coils. However, this may make the coils complex in structure, and the connection and fixation of the components thereof would be difficult.

Therefore, there is a need for a novel embolization member, which can solve the aforementioned problems.

SUMMARY OF THE INVENTION

The present invention provides an embolization member and a method for fabricating the embolization member. In addition to being clinically satisfactory in terms of visibility and able to be stably supported in an aneurysm, the embolization member can be at least partially degraded and absorbed by the body and transformed into small molecular substances that are harmless to the body, thus showing a reduced mass effect.

To this end, the embolization member provided in the present invention comprises a tubular first helical member including a lumen, a second helical member sleeved over an outer surface of the first helical member and a securing member at least partially disposed within the lumen of the first helical member, wherein the first helical member comprises a radiopaque material, wherein the second helical member comprises a bioabsorbable material, and wherein opposite ends of the securing member is coupled to respective opposite ends of the second helical member, so as to secure the first helical member to the second helical member.

Optionally, the first helical member may comprise a radiopaque material, and the second helical member may include a bioabsorbable material.

Optionally, the first helical member may be a metal member made of one of platinum, iridium, gold, silver, tantalum and tungsten, or an alloy thereof.

Optionally, the first helical member may be a composite material member made of a matrix incorporating a developing substance, wherein the developing substance is an iodine contrast agent or barium sulfate, and wherein the matrix is any one or more of polylactic acid, poly(glycolic acid), poly(lactic acid-co-glycolic acid), polydioxanone, polycaprolactone, polyurethane, chitosan and hyaluronic acid.

Optionally, the second helical member may be any one or more of polylactic acid, poly(glycolic acid), poly(lactic acid-co-glycolic acid), polydioxanone, polycaprolactone, polyurethane, chitosan, hyaluronic acid, magnesium, magnesium alloy, iron and iron alloy.

Optionally, the securing member may be a polymer wire, which is any one or more of polypropylene, nylon, polyester, polylactic acid, poly(glycolic acid), poly(lactic acid-co-glycolic acid) and polycaprolactone.

Optionally, the polymer wire may be coupled to the opposite ends of the second helical member through physical binding or tying, thereby securing the first helical member to the second helical member.

Optionally, opposite ends of the polymer wire may be tied to respective opposite ends of the first helical member and to the respective opposite ends of the second helical member.

Optionally, the polymer wire may be tied to at least one helical turn of the first helical member and at least one helical turn of the second helical member.

Optionally, at least one helical turn of the first helical member and at least one helical turn of the second helical member may be bound and tied by the polymer wire so as to keep the first helical member coaxial with or axially parallel to the second helical member.

Optionally, the first helical member may comprise a first helical unit and a second helical unit which is coaxial with or axially parallel to the first helical unit.

Optionally, the securing member may be a polymer wire, which is passed through lumens formed respectively by the first helical unit and the second helical unit, wherein portions of the polymer wire extend out of the first helical unit and the second helical unit are coupled to the second helical member, so as to secure the first helical unit and the second helical unit to the second helical member.

Optionally, the securing member may be a cured adhesive disposed between the first helical member and the second helical member and at least partially disposed within the lumen of the first helical member, so as to secure the first helical member to the second helical member.

Optionally, the securing member may comprise a first cured adhesive and a second cured adhesive, which are respectively disposed at the opposite ends of the second helical member.

Optionally, the securing member may further comprise a third cured adhesive disposed at any location between the first cured adhesive and the second cured adhesive.

Optionally, the first helical member and the second helical member may be coaxial with or axially parallel to each other. Alternatively or additionally, an axial length of the first helical member may be not greater than an axial length of the second helical member.

Optionally, at least one end of the second helical member may be closed with a domed cap formed by a hot melt adhesive or a dispensing glue, wherein an end of the first helical member is also wrapped in the domed cap.

Optionally, at least a portion of the securing member near the end of the second helical member may be also wrapped in the domed cap.

Optionally, the embolization member may further comprise a shaping member at least partially disposed within the lumen of the first helical member, the shaping member wrapped at one end in the domed cap.

Optionally, the shaping member may comprise at least one shaping wire each having a circular, oval or polygonal cross-sectional shape.

Optionally, the shaping member may be formed of any one or more of a cobalt-chromium alloy, a nickel-titanium alloy and a platinum-tungsten alloy.

Optionally, the shaping member may have at least one of helical, wavy, tetrahedral, pentahedral and hexahedral secondary shaping structures.

Optionally, the second helical member may be tubular and have an outer diameter ranging from 0.005 inches to 0.05 inches and a length ranging from 0.5 cm to 200 cm, wherein the second helical member is wound by wire having a cross-section in the shape of a circle or a part of a circle, and wherein a diameter of the wire or a size equal to two times a radius of curvature of the wire ranges from 0.0005 inches to 0.005 inches.

Optionally, the tubular first helical member may have an outer diameter ranging from 0.002 inches to 0.02 inches and a length equal to 10% to 100% of the length of the tubular second helical member, wherein the first helical member is wound by a wire having a cross-section in the shape of a circle or a part of a circle, and wherein a diameter of the wire or a size equal to two times a radius of curvature of the wire ranges from 0.0003 inches to 0.003 inches.

To the above end, the present invention provides another embolization member comprising a tubular first helical member comprising a lumen, a second helical member wound on an outer surface of the first helical member, a shaping member at least partially disposed within the lumen of the first helical member and a securing member at least partially disposed within the lumen of the first helical member, wherein: the first helical member comprises a radiopaque material and the second helical member comprises a bioabsorbable material; the securing member is coupled to opposite ends of the second helical member through physical binding or tying; one end of the shaping member is secured to one end of the first helical member and one end of the second helical member; and at least one end of the second helical member is closed with a domed cap formed by hot melt adhesive or dispensing glue, and in which the first helical member and the shaping member are at least partially wrapped.

To the above end, the method provided in the present invention comprises the steps of: pre-shaping the first helical member that has been coiled into a predetermined shape in a mold; disposing the securing member in the lumen of the first helical member; and sleeving the second helical member that has been coiled over the first helical member that has been coiled.

Optionally, the method may further comprise: pre-shaping the shaping member that has been coiled into a predetermined shape in a mold; disposing the pre-shaped shaping member in the lumen of the pre-shaped first helical member; coupling the securing member disposed in the lumen of the first helical member to opposite ends of the first helical member and opposite ends of the second helical member through physical binding or tying; and securing an end of the shaping member to an end of the first helical member and an end of the second helical member.

Optionally, the polymer wire may be tied to the first helical member and the second helical member in such a manner that: the polymer wire is first tied to at least one helical turn of the inner first helical member and then to at least one helical turn of the outer second helical member.

Optionally, the polymer wire may be tied to the first helical member and the second helical member in such a manner that: the polymer wire is simultaneously tied to at least one helical turn of the first helical member and at least one helical turn of the second helical member, as to keep the first helical member coaxial with or axially parallel to the second helical member.

In summary, the embolization members and the method provided in the present invention have the advantages as follows:

First, the embolization members are double-layer structures incorporating both the bioabsorbable material and the radiopaque metal material. As a result, the embolization members are enabled to maintain good radiographic visibility, support performance and other properties comparable to those of conventional metal coils, while being partially degradable and absorbable within a certain period of time due to the presence of the bioabsorbable material, thereby effectively mitigating its possible mass effect on the surrounding tissues and nerves and other problems.

Second, reasonable connection and fixation are designed between the various components in the double-layer helical structures of the embolization members, so that the two layers therein are substantially coaxial with or axially parallel to each other, effectively facilitating manipulation of surgeons during their use of the embolization members.

Figure 1:
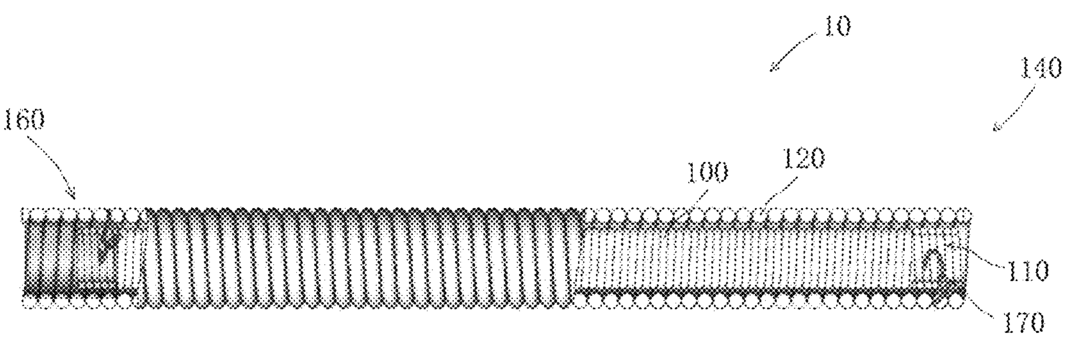
FIG. 1 is a cross-sectional view of a part of an embolization member according to a first embodiment of the present invention.

10, an embolization member; 100, a first helical member; 102, a first helical unit; 104, a second helical unit; 106, a third helical unit; 110, a lumen; 120, a second helical member; 130, a shaping member; 132, a distal end of the shaping member; 134, a proximal end of the shaping member; 140, a distal end; 150, a domed cap; 160, a proximal end; 170, a securing member; 171, 173, 175 portions of a polymer wire located outside of first and second helical units; 172, a first cured adhesive; 174, a second cured adhesive; 176, a third cured adhesive; 177, a distal end of the securing member; and 179, a proximal end of the securing member.

DETAILED DESCRIPTION

Objects, advantages and features of the present invention will become more apparent upon reading the following more detailed description of the present invention, which is made with reference to the accompanying drawings. Note that the figures are provided in a very simplified form not necessarily drawn to exact scale and for the only purpose of facilitating easy and clear description of the embodiments.

As used herein, the singular forms "a", "an" and "the" include plural referents, and the term "plurality" is employed in the sense of "two or more", unless the context clearly dictates otherwise. As used herein, the term "or" is generally employed in the sense of "and/or", unless the context clearly dictates otherwise. The terms "mounting", "coupling" and "connection" should be interpreted in a broad sense. For example, a connection may be a permanent, detachable or integral connection, or a mechanical or electrical connection, or a direct or indirect connection with one or more intervening media, or an internal communication or interaction between two elements. Those of ordinary skill in the art can understand the specific meanings of the above-mentioned terms herein, depending on their context. Throughout the annexed figures, like numerals indicate like elements.

In the following, for ease of description, the terms "distal end" and "proximal end" are used. The term "proximal end" refers to an end of a medical device closer to an operator who is operating the device, and the term "distal end" refers to an end of the medical device away from the operator. The following description sets forth numerous specific details in order to provide a more thorough understanding of the present invention. However, it will be apparent to those skilled in the art that the present invention can be practiced without one or more of these specific details. In other instances, well-known technical features have not been described in order to avoid unnecessary obscuring of the invention.

In principle, the present invention seeks to provide an embolization member including a tubular first helical member comprising a lumen, a second helical member sleeved over an outer surface of the first helical member and a securing member at least partially disposed within the lumen of the first helical member. The first helical member includes a radiopaque material, and the second helical member includes a bioabsorbable material. Opposite ends of the securing member are coupled to respective opposite ends of the second helical member, thereby securing the first helical member to the second helical member.

In order to achieve the above objects, the present invention provides another embolization member including a tubular first helical member comprising a lumen, a second helical member over wounded on an outer surface of the first helical member, a shaping member at least partially disposed within the lumen of the first helical member and a securing member at least partially disposed within the lumen of the first helical member. The first helical member includes a radiopaque material, and the second helical member includes a bioabsorbable material. The securing member is coupled to opposite ends of the second helical member by physical binding or tying. One end of the shaping member is secured to the first or second helical member, and at least one end of the second helical member is closed with a domed cap formed by a hot melt adhesive or dispensing glue, and the first helical member and the shaping member are at least partially wrapped in the domed cap.

It would be appreciated that the embolization member according to the present application may be a coil for treating intracranial vascular disease such as an intracranial aneurysm. Alternatively, this vascular implant may be used in the treatment of non-intracranial aneurysm or other disease.

After the embolization member is deployed in a lesion for a certain period of time, the biological material in the double-layer structure can be gradually degraded and absorbed by the body and transformed into small molecular substances that are harmless to the body, thus showing a reduced mass effect. Moreover, the securing member is provided in the double-layer helical structure, with reasonable connection and fixation being designed between the various components, the securing member and the double-layer structure are substantially coaxial with or axially parallel to each other, effectively facilitating manipulation of a surgeon during his/her use of the embolization member.

The embolization member and method proposed in the present invention will be described in greater detail below with reference to the accompanying drawing and several embodiments.

Figure 2:
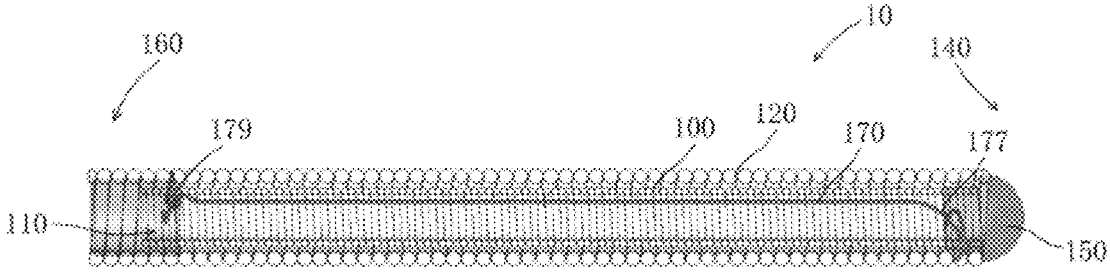
FIG. 2 is a cross-sectional view of the embolization member of FIG. 1.

FIG. 1 is a cross-sectional view of a part of an embolization member 10 according to a first embodiment of the present invention. FIG. 2 is a cross-sectional view of the embolization member 10 of FIG. 1. In the figures, the embolization member 10 comprises a linear initial shape. The embolization member 10 is a very long elongate device extending from a proximal end 160 to a distal end 140 thereof. The proximal end 160 of the embolization member 10 is configured for connection with a push device (not shown) for the embolization member 10. The embolization member 10 includes a tubular first helical member 100 comprising a lumen 110, a second helical member 120 sleeved over an outer surface of the first helical member 100 and a securing member 170 at least partially disposed within the lumen 110 of the first helical member 100. The first helical member 100, the second helical member 120 and the shaping member 170 are substantially coaxial with or axially parallel to one another. Opposite ends of the securing member 170 are coupled to respective opposite ends of the second helical member 120, thereby securing the first helical member 100 to the second helical member 120.

The first helical member 100 includes a radiopaque material. In some embodiments, the first helical member 100 is a metal member made of one of platinum, iridium, gold, silver, tantalum and tungsten, or an alloy thereof. The first helical member 100 may be formed by helically winding a metal wire made of the above material on a core bar of a predetermined diameter. Coil turns of the first helical member 100 may be spaced at a constant or varying pitch across the length of the coil, or at different pitches in different sections of the coil.

In some embodiments, the first helical member 100 is a composite material member formed of a matrix incorporating a developing substance. The developing substance may be an iodine contrast agent or barium sulfate. The matrix may be one or more of polylactic acid (PLA), poly(glycolic acid) (PGA), poly(lactic acid-co-glycolic acid) (PLGA), polydioxanone (PDO), polycaprolactone (PCL), polyurethane (PU), chitosan and hyaluronic acid. The first helical member 100 may be formed by helically winding a wire made of the composite material member on a core bar of a predetermined diameter.

In some embodiments, the bioabsorbable material included in the second helical member 120 may be one or more of PLA, PGA, PLGA, PDO, PCL, PU, chitosan, hyaluronic acid, magnesium, magnesium alloy, iron and iron alloy. In some embodiments, the second helical member 120 may be modified, for example, by adding some active substances into or onto the second helical member 120, such as growth factors or certain drug molecules. The second helical member 120 may be formed by helically winding a polymeric or metallic wire of the aforementioned material on a core bar of a predetermined diameter. It would be appreciated that coil turns of the second helical member 120 may be spaced at a constant or varying pitch across the length of the coil, or at different pitches in different sections of the coil.

A percentage of a volume of the second helical member 120 made of the bioabsorbable material in a total volume of the embolization member 10 may range from 30% to 90%. The double-layer structure made of both the bioabsorbable material and the radiopaque metal material enables the embolization member 10 to maintain good radiographic visibility, support performance and other properties comparable to those of conventional metal coils, while allowing the embolization member to be partially degraded and absorbed within a certain period of time due to the presence of the bioabsorbable material, thereby effectively mitigating its possible mass effect on the surrounding tissues and nerves and other problems.

In some embodiments, the first helical member 100 has an outer diameter ranging from 0.002 inches to 0.02 inches, and a cross-section of the wire that makes up the first helical member 100 is a circle or a part of a circle. A diameter of the wire or a size that is equal to two times a radius of curvature of the wire ranges from 0.0003 inches to 0.003 inches. An outer diameter of the second helical member 120 ranges from 0.005 inches to 0.05 inches, and a cross-section of the wire that makes up the second helical member 120 is a circle or a part of a circle. A diameter of the wire or a size that is equal to two times a radius of curvature of the wire ranges from 0.0005 inches to 0.005 inches. With continued reference to FIGS. 1 and 2, the second helical member 120 surrounds the first helical member 100, and an axial length of the first helical member 100 is not greater than an axial length of the second helical member 120. The length of the second helical member 120 ranges from 0.5 cm to 200 cm, and the length of the first helical member 100 is slightly smaller than the length of the second helical member 120 and is 10%-100% of the length of the tubular structure formed by the second helical member 120.

As shown in FIG. 2, the securing member 170 may be a wire made of a polymer, which may be one or more of polypropylene (PP), polyester, nylon, PLA, PGA, PLGA and PCL. The polymer wire is coupled to the opposite ends of the first helical member 100 and of the second helical member 120 by physical binding or tying, thereby securing the first helical member 100 to the second helical member 120.

In some embodiments, the securing member 170 may be tied to both the first helical member 100 and the second helical member 120. Specifically, the securing member 170 may be tied to at least one helical turn of the first helical member 100 and at least one helical turn of the second helical member 120 to make sure that the first helical member 100 and the second helical member 120 are maintained substantially coaxial with or axially parallel to each other. It would be appreciated that the securing member 170 is not limited to being coupled to the first helical member 100 and/or the second helical member 120 at the locations as shown in FIG. 2 as it may be tied to the helical member(s) at any circumferential locations. In some other embodiments, the securing member 170 may be tied to the first helical member 100 and the second helical member 120 in such a manner that it is first tied to at least one helical turn of the inner first helical member 100 and then to at least one helical turn of the outer second helical member 120.

In some embodiments, the securing member 170 may be alternatively tied to the first helical member 100 and the second helical member 120 in such a manner that: at the opposite ends of the first helical member 100 and the second helical member 120, the securing member 170 is tied to only at least one helical turn of the first helical member 100 or at least one helical turn of the second helical member 120.

With continued reference to FIG. 2, a non-invasive distal tip is formed at distal ends 140 of the first helical member 100 and the second helical member 120 by a hot melt adhesive or dispensing glue, thereby firmly bonding a distal end 177 of the securing member 170 to at least a part of the distal ends 140 of the first helical member 100 and the second helical member 120. The non-invasive distal tip may be a domed cap 150 as shown in FIG. 2, or a conical or oval closure structure. The distal ends 140 of the first helical member 100 and the second helical member 120 may be at least partially wrapped in the domed cap 150. The non-invasive distal tip may be formed of a polymeric material, such as polyester, an acrylic adhesive or another polymeric material suitable for use as the hot melt adhesive or dispensing glue. In some embodiments, the portion of the securing member 170 tied to the second helical member 120 may be also at least partially wrapped in the domed cap 150. In some other embodiments, another non-invasive tip may be formed at proximal ends 160 of the first helical member 100 and the second helical member 120 by a hot melt adhesive or dispensing glue, thereby firmly bonding a proximal end 179 of the securing member 170 to at least a part of the proximal end(s) 160 of the first helical member 100 and/or the second helical member 120.

Figure 3:
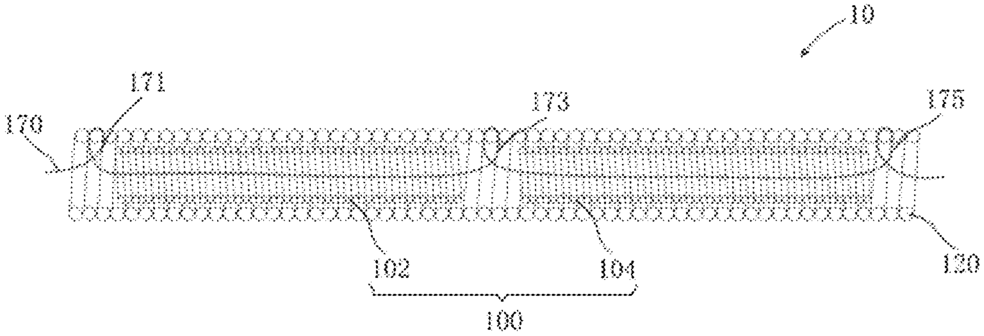
FIG. 3 is a cross-sectional view of an embolization member according to a second embodiment of the present invention.

FIG. 3 is a cross-sectional view of an embolization member 10 according to a second embodiment of the present invention. The embolization member 10 includes a tubular first helical member 100 comprising a lumen 110, a second helical member 120 sleeved over an outer surface of the first helical member 100 and a securing member 170 at least partially disposed within the lumen 110 of the first helical member 100. The first helical member 100 includes a first helical unit 102 and a second helical unit 104, which are substantially coaxial with or axially parallel to each other. In some embodiments, the securing member 170 is a polymer wire which is passed through lumens respectively formed by the first helical unit 102 and the second helical unit 104. Sections 171, 173 and 175 of the polymer wire located outside of the first helical unit 102 and the second helical unit 104 are coupled to the second helical member 120 at respective locations, thereby securing the first helical unit and the second helical unit 102, 104 to the second helical member 120. It would be appreciated that the first helical member 100 may alternatively have three, four, five or more helical units.

Figure 4:
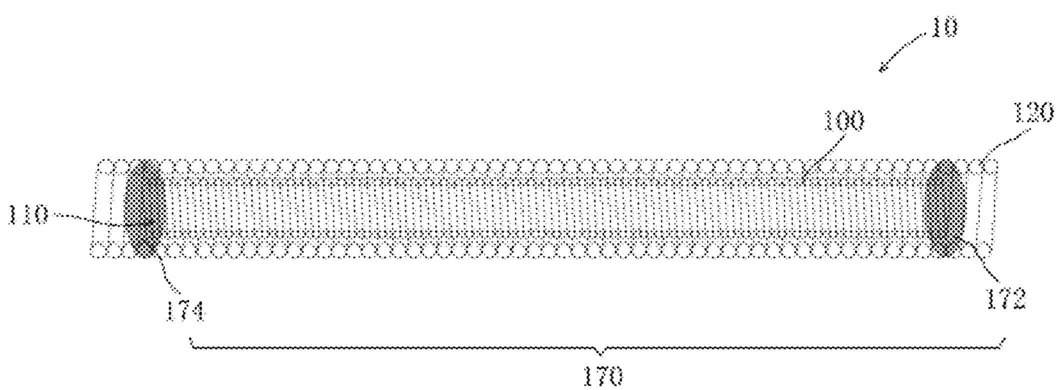
FIG. 4 is a cross-sectional view of an embolization member according to a third embodiment of the present invention.

FIG. 4 is a cross-sectional view of an embolization member 10 according to a third embodiment of the present invention. The embolization member 10 includes a tubular first helical member 100 comprising a lumen 110, a second helical member 120 sleeved over an outer surface of the first helical member 100 and a securing member 170 at least partially disposed within the lumen 110 of the first helical member 100. The securing member 170 includes a first cured adhesive 172 and a second cured adhesive 174, which are both disposed between the first helical member 100 and the second helical member 120 and at least partially disposed within the lumen 110 of the first helical member, thereby securing the first helical member 100 to the second helical member. In the illustrated embodiment, the first cured adhesive 172 and the second cured adhesive 174 are provided respectively at opposite ends of the second helical member 120, and respectively at least partially wrap opposite ends of the first helical member 100, thereby securing the first helical member 100 to the second helical member 120. It would be appreciated that both the first cured adhesive 172 and the second cured adhesive 174 may be dispensed on an exterior of the second helical member 120. The first cured adhesive 172 may be dispensed over an entire circumference of the second helical member 120, or dispensed over at least one location on the exterior of the second helical member 120.

In some embodiments, the securing member may further include a third cured adhesive, which may be disposed at any location between the first cured adhesive 172 and the second cured adhesive 174 and coupled to both the first helical member 100 and the second helical member 120, thereby securing the first helical member 100 to the second helical member 120.

Figure 5:
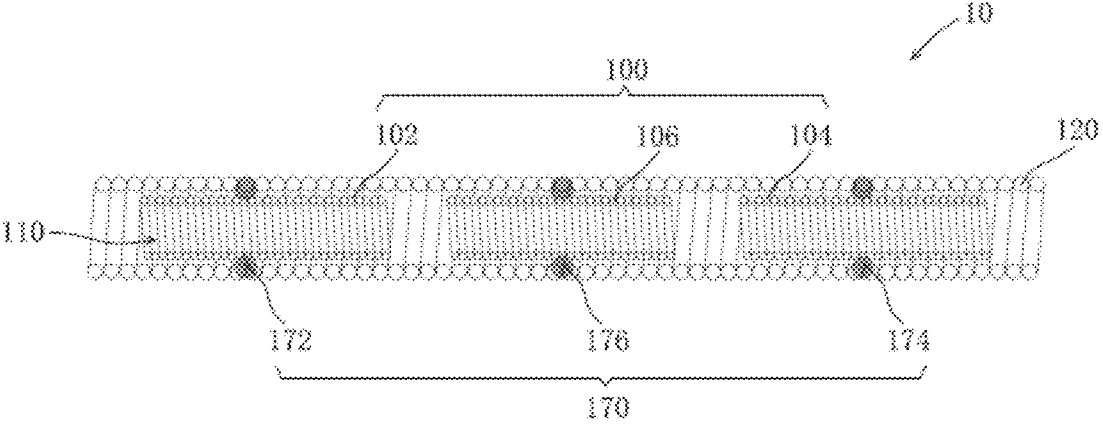
FIG. 5 is a cross-sectional view of an embolization member according to a fourth embodiment of the present invention.

FIG. 5 is a cross-sectional view of an embolization member 10 according to a fourth embodiment of the present invention. Similar to the embodiment shown in FIG. 3, a first helical member 100 includes a first helical unit 102, a second helical unit 104 and a third helical unit 106, which are substantially coaxial with or axially parallel to one another. Moreover, a securing member 170 may include a first cured adhesive 172, a second cured adhesive 174 and a third cured adhesive 176. The first cured adhesive 172 and the second cured adhesive 174 may be disposed respectively between opposite ends of a second helical member 120 and the first helical unit 102 and the second helical unit 104, thereby securing the first helical unit 102 and the second helical unit 104 to the second helical member 120. Moreover, the third cured adhesive 176 may be disposed between the second helical member 120 and the third helical unit 106, thereby securing the third helical unit 106 to the second helical member 120. In other embodiments, the numbers of the helical units and the cured adhesives are not so limited.

Figure 6:
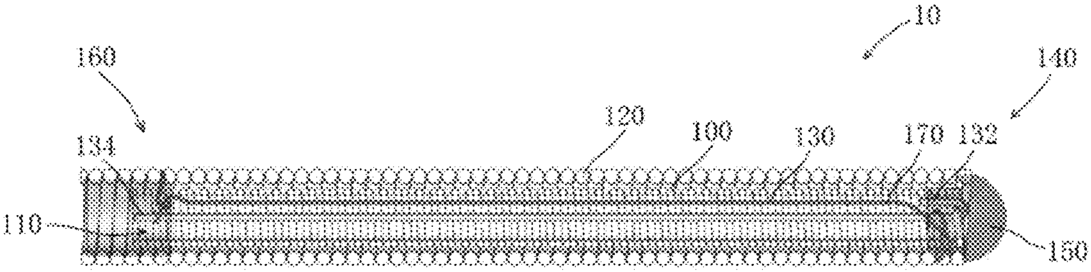
FIG. 6 is a cross-sectional view of an embolization member according to a fifth embodiment of the present invention.

FIG. 6 is a cross-sectional view of an embolization member 10 according to a fifth embodiment of the present invention. The embolization member 10 includes a tubular first helical member 100 comprising a lumen 110, a second helical member 120 sleeved over an outer surface of the first helical member 100, a shaping member 130 at least partially disposed within the lumen 110 of the first helical member 100 and a securing member 170 at least partially disposed within the lumen 110 of the first helical member 100. The first helical member 100, the second helical member 120 and the securing member 170 are structured and used substantially in the same way as in the embodiment shown in FIG. 2 and, therefore, need not be described in further detail herein. In some embodiments, the shaping member 130 may be substantially coaxial with or axially parallel to the first helical member 100.

As shown in FIG. 6, a distal end 132 of the shaping member 130 may be secured to distal ends 140 of the first helical member 100 and the second helical member 120, and a proximal end 134 of the shaping member 130 may be a free end disposed within the lumen 110 of the first helical member 100 around a proximal end thereof. In one embodiment of the present application, the shaping member 130 may comprise an inverted J-shaped hook at the distal end 132, which may be coupled to at least one coil turn of the first helical member 100 around the distal end 140, such as the most distal coil turn. Moreover, a non-invasive distal tip may be formed by a hot melt adhesive or dispensing glue at the distal ends 140 of the first helical member 100 and the second helical member 120, thereby firmly bonding the distal end 132 of the shaping member 130 to the distal ends 140 of the first helical member 100 and the second helical member 120. That is, at least a part of the inverted J-shaped hook, and the distal ends 140 of the first helical member 100 and the second helical member 120 may be wrapped in the non-invasive distal tip. The non-invasive distal tip may be a domed cap 150 as shown in FIG. 2, or a conical or oval closure structure. The non-invasive distal tip may be formed of a polymeric material, such as polyester, an acrylic adhesive or another polymeric material suitable for use as the hot melt adhesive or dispensing glue. In some other embodiments, the distal end 132 of the shaping member 130 may be otherwise coupled to the distal ends 140 of the first helical member 100 and the second helical member 120. For example, the distal end 132 of the shaping member 130 may be straight, inverted J-shaped or otherwise shaped and directly wrapped and secured by the domed cap 150. Alternatively, the distal end 132 of the shaping member 130 may be first coupled to at least one coil turn of the second helical member 120 and then wrapped and secured by the domed cap 150. Still alternatively, the shaping member 130 may be coupled to at least one end of each of the first helical member 100 and the second helical member 120 by physical binding or tying.

In some embodiments, the proximal end 134 of the shaping member 130 may be coupled to a proximal end 160 of the first helical member 100, and the distal end 132 may be free. Alternatively, the proximal end 134 and the distal end 132 may be coupled to the proximal end 160 and the distal end 140 of the first helical member 100, respectively.

In some embodiments, the shaping member 130 may include at least one shaping wire each having a circular, oval or polygonal cross-section and a diameter not exceeding 90% of an inner diameter of the first helical member 100, wherein an inner diameter of the first helical member ranges from 0.001 inches to 0.01 inches. The shaping member 130 may be formed of a memory alloy, which may be one or more of cobalt-chromium, nickel-titanium and platinum-tungsten alloys. The shaping member 130 made of such a material can improve radiographic visibility of the double-layer helical structure in a blood vessel or aneurysm, and the shape memory alloy may be pre-shaped three-dimensionally to enhance stability of the embolization member 10 and enable the embolization member to have better support performance within an aneurysm. In some embodiments, the shaping member 130 may be pre-shaped so as to have at least one of helical, wavy, tetrahedral, pentahedral and hexahedral secondary structures.

In order to achieve the above objects, the present invention further provides a method for fabricating an embolization member 10. Referring to FIG. 6, the method essentially includes the steps of:

S1: pre-shaping a wound first helical member 100 and a wound shaping member 130 in molds into predetermined shapes, each of which may consist of at least one of helical, wavy, tetrahedral, pentahedral and hexahedral shapes, and the predetermined shape of the first helical member 100 corresponds to the predetermined shape of shaping member 130;

S2: disposing the pre-shaped shaping member 130 in a lumen 110 formed by the pre-shaped first helical member 100, i.e., inserting the shaping member 130 that is in the shape of a wire through the lumen 110 of the first helical member 100 and securing at least one end of the shaping member 130 to at least one end of the first helical member 100;

S3: disposing the securing member 170 in the lumen 110 of the first helical member 100;

S4: sleeving a wound second helical member 120 over the coiled first helical member 100; and S5: coupling the securing member 170 disposed in the lumen 110 of the first helical member 100 to opposite ends of the first helical member 100 and opposite ends of the second helical member 120 through physical binding or tying, and closing at least one end of the second helical member 120 by forming a domed cap 150 there using a hot melt adhesive or dispensing glue, wherein the first helical member 100 and the shaping member 130 are both at least partially wrapped in the domed cap 150.

Although the present invention has been disclosed hereinabove, it is not limited to the above disclosure. Those skilled in the art can make various changes and modifications to the invention without departing from the spirit and scope thereof.

What is claimed is:

1. An embolization member, comprising a tubular first helical member including a lumen, a second helical member sleeved over an outer surface of the first helical member and a securing member at least partially disposed within the lumen of the first helical member, wherein the first helical member comprises a radiopaque material, wherein the second helical member comprises a bioabsorbable material, and wherein opposite ends of the securing member are respectively coupled to opposite ends of the second helical member, so as to secure the first helical member to the second helical member, wherein an axial length of the first helical member is less than an axial length of the second helical member.

2. The embolization member of claim 1, wherein the first helical member is a metal member made of one of platinum, iridium, gold, silver, tantalum and tungsten, or an alloy thereof.

3. The embolization member of claim 1, wherein the first helical member is a composite material member made of a matrix incorporating a developing substance, wherein the developing substance is an iodine contrast agent or barium sulfate, and wherein the matrix is any one or more of polylactic acid, poly(glycolic acid), poly(lactic acid-co-glycolic acid), polydioxanone, polycaprolactone, polyurethane, chitosan and hyaluronic acid.

4. The embolization member of claim 1, wherein the second helical member is any one or more of polylactic acid, poly(glycolic acid), poly(lactic acid-co-glycolic acid), polydioxanone, polycaprolactone, polyurethane, chitosan, hyaluronic acid, magnesium, magnesium alloy, iron and iron alloy.

5. The embolization member of claim 1, wherein the securing member is a polymer wire, and wherein the polymer wire is any one or more of polypropylene, nylon, polyester, polylactic acid, poly(glycolic acid), poly(lactic acid-co-glycolic acid) and polycaprolactone.

6. The embolization member of claim 5, wherein the polymer wire is coupled to the opposite ends of the second helical member through a physical binding or a tying, so as to secure the first helical member to the second helical member, and wherein opposite ends of the polymer wire are tied to opposite ends of the first helical member and the opposite ends of the second helical member respectively.

7. The embolization member of claim 6, wherein the polymer wire is tied to at least one helical turn of the first helical member and at least one helical turn of the second helical member respectively; or wherein at least one helical turn of the first helical member and at least one helical turn of the second helical member are bound and tied by the polymer wire, so as to keep the first helical member coaxial with or axially parallel to the second helical member.

8. The embolization member of claim 1, wherein the first helical member comprises a first helical unit and a second helical unit which is coaxial with or axially parallel to the first helical unit, wherein the first helical unit and the second helical unit are disconnected with a gap provided therebetween, wherein the securing member is a polymer wire, which is passed through lumens formed by the first helical unit and the second helical unit, and wherein portions of the polymer wire extending out of opposite ends of the first helical unit and opposite ends of the second helical unit are coupled to the second helical member, so as to secure the first helical unit and the second helical unit to the second helical member.

9. The embolization member of claim 1, wherein the securing member is a cured adhesive disposed between the first helical member and the second helical member, and at least partially disposed within the lumen of the first helical member, so as to secure the first helical member to the second helical member, wherein the securing member comprises a first cured adhesive and a second cured adhesive, which are respectively disposed at the opposite ends of the second helical member, and wherein the securing member further comprises a third cured adhesive disposed at any location between the first cured adhesive and the second cured adhesive.

10. The embolization member of claim 1, wherein the first helical member is coaxial with or axially parallel to the second helical member.

11. The embolization member of claim 1, wherein at least one end of the opposite ends of the second helical member is closed with a domed cap formed by a hot melt adhesive or a dispensing glue, wherein an end of the first helical member is also wrapped in the domed cap.

12. The embolization member of claim 11, wherein at least a portion of the securing member near the at least one end of the opposite ends of the second helical member is also wrapped in the domed cap.

13. The embolization member of claim 11, further comprising a shaping member at least partially disposed within the lumen of the first helical member, wherein an end of the shaping member is wrapped in the domed cap.

14. The embolization member of claim 13, wherein the shaping member comprises at least one shaping wire each having a circular cross-sectional shape, an oval cross-sectional shape or a polygonal cross-sectional shape; and/or wherein the shaping member is formed of any one or more of a cobalt-chromium alloy, a nickel-titanium alloy and a platinum-tungsten alloy; and/or wherein the shaping member has at least one of helical, wavy, tetrahedral, pentahedral and hexahedral secondary shaping structures.

15. The embolization member of claim 1, wherein the second helical member is tubular and has an outer diameter ranging from 0.005 inches to 0.05 inches and a length ranging from 0.5 cm to 200 cm, wherein the second helical member is wound by a wire having a cross-section in a shape of a circle or a part of a circle, and wherein a diameter of the wire or a size equal to two times a radius of curvature of the wire ranges from 0.0005 inches to 0.005 inches.

16. The embolization member of claim 15, wherein the first helical member that is tubular has an outer diameter ranging from 0.002 inches to 0.02 inches and a length equal to 10% to 100% of the length of the tubular second helical member, wherein the first helical member is wound by a wire having a cross-section in a shape of a circle or a part of a circle, and wherein a diameter of the wire or a size equal to two times a radius of curvature of the wire ranges from 0.0003 inches to 0.003 inches.

17. A method for fabricating the embolization member of claim 1, comprising the steps of:

pre-shaping the first helical member that has been coiled into a predetermined shape in a mold;

disposing the securing member in the lumen of the first helical member; and sleeving the second helical member that has been coiled over the first helical member that has been coiled.

18. The method of claim 17, further comprising:

pre-shaping a shaping member that has been coiled into a predetermined shape in a mold;

disposing the pre-shaped shaping member in the lumen of the pre-shaped first helical member;

coupling the securing member disposed in the lumen of the first helical member to opposite ends of the first helical member and the opposite ends of the second helical member through physical binding or tying; and securing an end of the shaping member to an end of the opposite ends the first helical member and an end of the opposite ends the second helical member.

19. The method of claim 18, wherein the securing member is a polymer wire, and wherein the polymer wire is tied to the first helical member and the second helical member in such a manner that: the polymer wire is first tied to at least one helical turn of the inner first helical member and then to at least one helical turn of the outer second helical member; or wherein the polymer wire is tied to the first helical member and the second helical member in such a manner that: the polymer wire is simultaneously tied to at least one helical turn of the first helical member and at least one helical turn of the second helical member, so as to keep the first helical member coaxial with or axially parallel to the second helical member.

20. An embolization member comprising a tubular first helical member comprising a lumen, a second helical member sleeved over an outer surface of the first helical member, a shaping member at least partially disposed within the lumen of the first helical member and a securing member at least partially disposed within the lumen of the first helical member, wherein:

the first helical member comprises a radiopaque material and the second helical member comprises a bioabsorbable material;

the securing member is coupled to opposite ends of the second helical member through physical binding or tying;

an end of the shaping member is secured to an end of the first helical member and an end of the opposite ends of the second helical member; and at least one end of the opposite ends the second helical member is closed with a domed cap by forming a hot melt adhesive or a dispensing glue, and wherein the first helical member and the shaping member are at least partially wrapped in the domed cap, wherein an axial length of the first helical member is less than an axial length of the second helical member.

* * * * *